United States Patent
Burek

(10) Patent No.: US 10,478,397 B2
(45) Date of Patent: Nov. 19, 2019

(54) AVIAN TINCTURE

(71) Applicant: Susan Burek, Willis, MI (US)

(72) Inventor: Susan Burek, Willis, MI (US)

( * ) Notice: Subject to any disclaimer, the term of this patent is extended or adjusted under 35 U.S.C. 154(b) by 538 days.

(21) Appl. No.: 15/066,518

(22) Filed: Mar. 10, 2016

(65) Prior Publication Data

US 2016/0263028 A1 Sep. 15, 2016

Related U.S. Application Data

(60) Provisional application No. 62/130,653, filed on Mar. 10, 2015.

(51) Int. Cl.
| | |
|---|---|
| *A61K 36/00* | (2006.01) |
| *A61K 9/00* | (2006.01) |
| *A61K 36/28* | (2006.01) |
| *A61K 36/236* | (2006.01) |
| *A61K 36/81* | (2006.01) |
| *A61K 36/185* | (2006.01) |
| *A61K 36/53* | (2006.01) |
| *A61K 36/9066* | (2006.01) |
| *B65B 7/16* | (2006.01) |
| *A23K 10/30* | (2016.01) |
| *A23K 20/10* | (2016.01) |
| *A23K 50/75* | (2016.01) |
| *A61K 9/08* | (2006.01) |
| *A61K 36/8962* | (2006.01) |
| *A61K 36/9068* | (2006.01) |
| *A61K 36/38* | (2006.01) |
| *A61K 36/481* | (2006.01) |
| *A61K 36/70* | (2006.01) |
| *A23K 20/00* | (2016.01) |

(52) U.S. Cl.
CPC ............ *A61K 9/0095* (2013.01); *A23K 10/30* (2016.05); *A23K 20/00* (2016.05); *A23K 20/10* (2016.05); *A23K 50/75* (2016.05); *A61K 9/08* (2013.01); *A61K 36/185* (2013.01); *A61K 36/236* (2013.01); *A61K 36/28* (2013.01); *A61K 36/38* (2013.01); *A61K 36/481* (2013.01); *A61K 36/53* (2013.01); *A61K 36/70* (2013.01); *A61K 36/81* (2013.01); *A61K 36/8962* (2013.01); *A61K 36/9066* (2013.01); *A61K 36/9068* (2013.01); *B65B 7/16* (2013.01)

(58) Field of Classification Search
None
See application file for complete search history.

(56) References Cited

U.S. PATENT DOCUMENTS 8,342,446 B2  2/2013  Burek

OTHER PUBLICATIONS

Zhai et al. (2007) Food Agric. Immunol. 18(3-4): 221-236. (Year: 2007).*
Wendakoon et al. (2012) Journal of Medicinally Active Plants, vol. 1, Issue 2, 60-68. (Year: 2012).*
Tajik et al. (2008) Journal of Animal and Veterinary Advances, 7(4): 508-511. (Year: 2008).*
Saddiqe et al. (2010) Journal of Ethnopharmacology 131: 511-521. (Year: 2010).*
Website document entitled "Recommended Alcohol Percent for Tincuring" (available at https://permies.com/t/34663/kitchen/Recommended-Alcohol-Percent-Tincuring). Downloaded from website Oct. 23, 2018. (Year: 2014).*
Website document entitled "How to make a tincture" posed by Herbal Academy Feb. 3, 2014. Available at https://theherbalacademy.com/how-to-make-a-tincture. Downloaded Oct. 23, 2018. (Year: 2014).*
Website document entitled "Assessment report on Echinacea angustifolia DC., radix" Dated Mar. 27, 2012 (Year: 2012).*
Careaga et al. (2003) International Journal of Food Microbiology 83, 331-335. (Year: 2003).*
Al-Mola et al. (2007) J. Edu. Sci. vol. 19, No. 2, 11 pages (Year: 2007).*

* cited by examiner

*Primary Examiner* — Russell G Fiebig
(74) *Attorney, Agent, or Firm* — The Dobrusin Law Firm, PC

(57) ABSTRACT

An avian tincture composition and associated methods for producing the same for treatment of the avian species with the avian tincture. The avian tincture may be used in the treatment of abscesses, inflamed and swollen leg joints, respiratory issues, wounds, infection, and acute disease or parasite overload conditions.

9 Claims, No Drawings

AVIAN TINCTURE

FIELD

The present teachings relate to an avian tincture composition and methods for producing an avian tincture composition. The teachings further relate to methods for treatment of the avian species with the avian tincture composition.

BACKGROUND

Diseases of poultry are a major concern. Natural poultry keeping methods and holistic remedies for poultry can provide a safe alternative to treating poultry diseases. There is a desire in the poultry industry for methods to treat avian disease that are considered natural, herbal or organic remedies. See for example, U.S. Pat. No. 8,372,446, incorporated by reference herein. As such, it would be beneficial in the industry to develop natural avian treatments that promote the well-being of the avian species.

It would be beneficial to develop natural avian treatments that provide nutritive and health benefits. It would be beneficial to develop natural avian treatments that are able to treat a wide range of health problems. It would be further desirable that these treatments would include natural ingredients that are safe for poultry. The present teachings are directed to an avian tincture composition, methods for producing the avian tincture composition and methods for treatment of the avian species with the avian tincture composition. The avian tincture composition of the present teachings provides nutritive and health benefits and may be used in the treatment of abscesses, inflamed and swollen leg joints, respiratory issues, wounds, infection, and acute disease or parasite overload conditions.

SUMMARY

The present teachings contemplate a method for producing an avian tincture comprising: mixing a ratio of at least one fresh herb with a liquid including alcohol or mixing a ratio of at least one dried herb with a liquid including alcohol and water into a first container; sealing the first container to provide an air tight environment; shaking the mixture about 2-3 times a day for about 2 weeks; straining the herb material to separate it from the liquid mixture; pouring the liquid mixture into a second container; sealing the second container containing the liquid mixture and storing it.

The alcohol may be 190 proof neutral organic grain alcohol. The alcohol may be present in an amount of about 5% to about 95%. The alcohol may be present in an amount of about 50% to about 100%. The ratio of herbs to liquid may be 1:2 for fresh herbs and 1:5 for dried herbs. The herbs may be selected from the group consisting of: *Echinacea Purpea/augustifolia* (Purple Coneflower), *Hypericum perforatum* (St. John's Wort), *Ligusticum porter* (Osha Root), *Achillea millifolium* (Yarrow), *Anemopsis californicum* (Yerba Mansa), *Rumex crispus* (Yellow Dock), *Capsicum* (Cayenne), *Monarda fistulosa* (Bee Balm), *Arctium lappa* (Burdock), *Daucus carota* (Queen Anne's Lace), *Allium sativum* (Garlic) and any combination thereof.

*Echinacea Purpea/augistifolia* (Purple Coneflower) or *Ligusticum porter* (Osha Root) may be mixed with a liquid including about 70% alcohol and about 30% water. *Achillea millifolium* (Yarrow) or *Rumex crispus* (Yellow Dock) may be mixed with a liquid including about 50% alcohol and about 50% water. *Anemopsis californicum* (Yerba Mansa) or *Arctium lappa* (Burdock) or *Daucus carota* (Queen Anne's lace) may be mixed with a liquid including about 60% alcohol and about 40% water. *Capsicum* (cayenne) may be mixed with a liquid including about 95% alcohol and about 5% water.

The method may further include combining the avian tincture with one or more different avian tinctures into an avian tincture formula. The method may include combining tinctures of Yarrow, St. John's Wort, Yerba Mansa, Yellow Dock and Cayenne. The method may include combining tinctures of *Echinacea*, Goldenseal, St. John's Wort and Osha Root. The method may include combining tinctures of Yarrow, St. John's Wort and Cayenne. The method may include combining tinctures of Osha Root, Bee Balm, Burdock Root and Queen Anne's lace. The method may include combining tinctures of St. John's Wort, Bee Balm, and Garlic.

The present teachings also contemplate an avian composition comprising a mixture of least one extracted herb from the group consisting of *Echinacea Purpea/augustifolia* (Purple Coneflower), *Hypericum perforatum* (St. John's Wort), *Ligusticum porter* (Osha Root), *Achillea millifolium* (Yarrow), *Anemopsis californicum* (Yerba Mansa), *Rumex crispus* (Yellow Dock), *Capsicum* (Cayenne), *Monarda fistulosa* (Bee Balm), *Arctium lappa* (Burdock), *Daucus carota* (Queen Anne's Lace), *Allium sativum* (Garlic), Usnea, Oregano, Wormwood, Black Walnut, New England Aster, Bayberry, Oregon Grape, Ginger, *Astragulus*, Stinging Nettle, Tumeric and any combination thereof and about 50% to about 100% alcohol.

The present teachings also contemplate a method for treatment with the avian tincture compromising: administrating an internal dose of the avian tincture to a bird; monitoring health symptoms of the bird; and repeating the internal dose of tincture to the bird over a period of from about 5 to about 10 days. The present teachings also contemplate a method for treating the avian species with the avian tincture, wherein the method includes applying the avian tincture to an external wound or cyst of the bird.

The dose of tincture may be about 1 drop per pound of weight of the bird. A dose of about 6-10 drops per day may be administered. A high dose of about 10-15 drops per day may be administered. The method may include administering the high dose twice a day.

The present teachings are directed to an avian tincture composition, methods for producing an avian tincture composition and treatment of the avian species with the avian tincture composition. The present teachings promote the health and well-being of the avian species. The present teachings provide nutritive and health benefits. The present teachings provide for methods to treat avian disease that are considered natural, herbal and/or organic remedies. The present teachings provide for natural avian treatments that are able to treat a wide range of health problems. The avian tincture of the present teachings may be used in the treatment of abscesses, inflamed and swollen leg joints, respiratory issues, wounds, infection, and acute disease or parasite overload conditions. The avian tincture of the present teachings may be an antibacterial, anti-inflammatory, antimicrobial, expectorant, astringent, waste elimination stimulator, blood circulation stimulator, nutritive or any combination thereof. The present teachings provide for treatments that include natural ingredients that are safe for poultry.

DETAILED DESCRIPTION

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

This application claims the benefit of the filing date of U.S. Provisional Application No. 62/130,653 filed Mar. 10, 2015. The entirety of the contents of that application are hereby incorporated by reference for all purposes.

The present teachings contemplate an avian tincture composition and associated methods for producing the same for treatment of the avian species with the avian tincture. The avian tincture composition includes natural ingredients and provides nutritive and health benefits. The avian tincture may be used in the treatment of abscesses, inflamed and swollen leg joints, respiratory issues, wounds, infection, and acute disease or parasite overload conditions.

The present teachings contemplate a method for producing an avian tincture. The method may include mixing a ratio of at least one fresh herb with a liquid including alcohol into a first container. The method may include mixing a ratio of at least one dried herb with a liquid including alcohol and water into a first container. The method may include mixing a ratio of at least one fresh herb with a liquid including alcohol or mixing a ratio of at least one dried herb with a liquid including alcohol and water into a first container. The method may include mixing a ratio of dried herbs, fresh herbs, water and alcohol into a first container. Preferably, the herbs are chopped to aid in extraction. The first container may be plastic, ceramic or glass. The method may include sealing the first container to provide an air tight environment.

The method may include shaking the mixture over a period of time. The method may include shaking the mixture anywhere from 1 to 5 times a day for a period of about 8 hours to about 4 weeks. The method may include shaking the mixture once a day for about 1 week. The method may include shaking the mixture twice a day for about two weeks. Preferably, the method includes shaking the mixture for about 2-3 times a day for about 2 weeks.

The method may include straining the herb material to separate it from the liquid mixture. Preferably, the herb material is strained though a cheesecloth or metal strainer. The method may include pouring the liquid mixture into a second container. The second container may be plastic, ceramic or glass. The second container may include a dropper. Preferably, the liquid mixture is poured into a glass bottle. The glass bottle may be labeled and dated.

The method may include sealing the second container containing the liquid mixture and storing it. Preferably, the liquid mixture is stored in a dark or amber colored glass bottle. Preferably, the stored tincture is kept away from exposure to sunlight and heat. Preferably, the tincture is stored in a cool, dark environment.

The shelf life of the tincture may be at least about six months. The shelf life of the tincture may be at least one year. The shelf life of the tincture may be at least 2 years. The shelf life of the tincture of the tincture may be at least 3 years. The shelf life of a tincture stored in a cool dark environment may be indefinite.

The method includes mixing herbs with liquid. The liquid may include alcohol. The liquid may consist of alcohol. The alcohol may be 190 proof neutral organic grain alcohol. The alcohol may be diluted with water. The liquid may include alcohol and water. The liquid may consist of alcohol and water.

The ratio of alcohol to water may be 1:1. The ratio of alcohol to water may be 1:20. The ratio of alcohol to water may be 9:10. The ratio of alcohol to water may be 4:5. The ratio of alcohol to water may be 7:10. The ratio of alcohol to water may be 2:3. The ratio of alcohol to water may be 3:5. The ratio of alcohol to water may be 1:2. The ratio of alcohol to water may be 1:4.

Herbs (fresh and/or dried) may be mixed with a liquid. The liquid may include about 0.01% to about 100% alcohol. The ratio of herbs to liquid may be 1:2 for fresh herbs. The ratio of herbs to liquid may be 1:5 for dried herbs. Fresh herbs may be mixed with liquid including 100% alcohol. Dried herbs may be mixed with liquid including alcohol and water.

The alcohol may be present in an amount of about 5% to about 95% of the liquid. The alcohol may be present in an amount of about 50% to about 70% of the liquid. The liquid mixture of alcohol and water may include about 95% alcohol and about 5% water. The liquid mixture of alcohol and water may include about 70% alcohol and about 30% water. The liquid mixture of alcohol and water may include about 60% alcohol and about 40% water. The liquid mixture of alcohol and water may include about 50% alcohol and about 50% water. The liquid mixture of alcohol and water may include about 25% alcohol and about 75% water.

The herbs may be selected from the group consisting of: *Echinacea Purpea/augustifolia* (Purple Coneflower), *Hypericum perforatum* (St. John's Wort), *Ligusticum porter* (Osha Root), *Achillea millifolium* (Yarrow), *Anemopsis californicum* (Yerba Mansa), *Rumex crispus* (Yellow Dock), *Capsicum* (Cayenne), *Monarda fistulosa* (Bee Balm), *Arctium lappa* (Burdock), *Daucus carota* (Queen Anne's Lace), *Allium sativum* (Garlic), and any combination thereof. The herbs may be selected from the group consisting of: St. John's Wort, Usnea, Garlic, Yerba Mansa, Oregano, Wormwood, Black Walnut, *Echinacea*, New England Aster, Bayberry, Oregon Grape, Yellow Dock, Yarrow, Cayenne, Ginger, Burdock, *Astragulus*, Stinging Nettle, Tumeric and any combination thereof. The herbs may be selected from the group consisting of: *Echinacea Purpea/augustifolia* (Purple Coneflower), *Hypericum perforatum* (St. John's Wort), *Ligusticum porter* (Osha Root), *Achillea millifolium* (Yarrow), *Anemopsis californicum* (Yerba Mansa), *Rumex crispus* (Yellow Dock), *Capsicum* (Cayenne), *Monarda fistulosa* (Bee Balm), *Arctium lappa* (Burdock), *Daucus carota* (Queen Anne's Lace), *Allium sativum* (Garlic), Usnea, Oregano, Wormwood, Black Walnut, New England Aster, Bayberry, Oregon Grape, Ginger, *Astragulus*, Stinging Nettle, Tumeric and any combination thereof. The ratio of a combination of herbs may be 1:1. The ratio of a combination of herbs may vary.

In some non-limiting examples, an herb selected from *Echinacea Purpea/augustifolia* (Purple Coneflower), *Ligusticum porter* (Osha Root), *Achillea millifolium* (Yarrow), *Rumex crispus* (Yellow Dock), *Anemopsis californicum* (Yerba Mansa), *Arctium lappa* (Burdock), *Daucus carota* (Queen Anne's Lace), *Capsicum* (cayenne), *Hypericum per-* foratum (St. John's Wort), *Monarda fistulosa* (Bee Balm), *Allium sativum* (Garlic) and any combination thereof may be mixed with a liquid including from about 50% to about 100% alcohol.

In an example, *Echinacea Purpea/augistifolia* (Purple Coneflower) may be selected as the herb in the avian tincture. Preferably, the roots and flowers of *Echinacea Purpea/augistifolia* (Purple Coneflower) are used. *Echinacea Purpea/augistifolia* (Purple Coneflower) may be mixed with a liquid including from about 50% to about 100% alcohol. The ratio of *Echinacea Purpea/augistifolia* (Purple Coneflower) to liquid may be 1:2 if fresh herbs are used. The ratio of *Echinacea Purpea/augistifolia* (Purple Coneflower) to liquid may be 1:5 if dried herbs are used. If dried *Echinacea Purpea/augistifolia* (Purple Coneflower) is used, preferably it is mixed with a liquid including about 70% alcohol and about 30% water.

In an example, *Ligusticum porter* (Osha Root) may be selected as the herb in the avian tincture. *Ligusticum porter* (Osha Root) may be mixed with a liquid including from about 50% to about 100% alcohol. Preferably, the root of *Ligusticum porter* (Osha Root) is used. The ratio of *Ligusticum porter* (Osha Root) to liquid may be 1:2 if fresh herbs are used. The ratio of *Ligusticum porter* (Osha Root) to liquid may be 1:5 if dried herbs are used. If dried *Ligusticum porter* (Osha Root) is used, preferably it is mixed with a liquid including about 70% alcohol and about 30% water.

In an example, *Achillea millifolium* (Yarrow) may be selected as the herb in the avian tincture. *Achillea millifolium* (Yarrow) may be mixed with a liquid including from about 50% to about 100% alcohol. Preferably, the leaves and flowers of *Achillea millifolium* (Yarrow) are used. The ratio of *Achillea millifolium* (Yarrow) to liquid may be 1:2 if fresh herbs are used. The ratio of *Achillea millifolium* (Yarrow) to liquid may be 1:5 if dried herbs are used. If dried *Achillea millifolium* (Yarrow) is used, preferably it is mixed with a liquid including about 50% alcohol and about 50% water.

In an example, *Rumex crispus* (Yellow Dock) may be selected as the herb in the avian tincture. *Rumex crispus* (Yellow Dock) may be mixed with a liquid including from about 50% to about 100% alcohol. Preferably, the root of *Rumex crispus* (Yellow Dock) is used. The ratio of *Rumex crispus* (Yellow Dock) to liquid may be 1:2 if fresh herbs are used. The ratio of *Rumex crispus* (Yellow Dock) to liquid may be 1:5 if dried herbs are used. If dried *Rumex crispus* (Yellow Dock) is used, preferably it is mixed with a liquid including about 50% alcohol and about 50% water.

In an example, *Anemopsis californicum* (Yerba Mansa) may be selected as the herb in the avian tincture. *Anemopsis californicum* (Yerba Mansa) may be mixed with a liquid including from about 50% to about 100% alcohol. Preferably, the leaves and the flowers of *Anemopsis californicum* (Yerba Mansa) are used. The ratio of *Anemopsis californicum* (Yerba Mansa) to liquid may be 1:2 if fresh herbs are used. The ratio of *Anemopsis californicum* (Yerba Mansa) to liquid may be 1:5 if dried herbs are used. If dried *Anemopsis californicum* (Yerba Mansa) is used, preferably it is mixed with a liquid including about 60% alcohol and about 40% water.

In an example, *Arctium lappa* (Burdock) may be selected as the herb in the avian tincture. *Arctium lappa* (Burdock) may be mixed with a liquid including from about 50% to about 100% alcohol. Preferably, the root of *Arctium lappa* (Burdock) is used. The ratio of *Arctium lappa* (Burdock) to liquid may be 1:2 if fresh herbs are used. The ratio of *Arctium lappa* (Burdock) to liquid may be 1:5 if dried herbs are used. If dried *Arctium lappa* (Burdock) is used, preferably it is mixed with a liquid including about 60% alcohol and about 40% water.

In an example, *Daucus carota* (Queen Anne's Lace) may be selected as the herb in the avian tincture. *Daucus carota* (Queen Anne's Lace) may be mixed with a liquid including from about 50% to about 100% alcohol. Preferably, the leaves and flowers of *Daucus carota* (Queen Anne's Lace) are used. The ratio of *Daucus carota* (Queen Anne's Lace) to liquid may be 1:2 if fresh herbs are used. The ratio of *Daucus carota* (Queen Anne's Lace) to liquid may be 1:5 if dried herbs are used. If dried *Daucus carota* (Queen Anne's Lace) is used, preferably it is mixed with a liquid including about 60% alcohol and about 40% water.

In an example, *Capsicum* (cayenne) may be selected as the herb in the avian tincture. *Capsicum* (cayenne) may be mixed with a liquid including from about 50% to about 100% alcohol. Preferably, the fruit of *capsicum* (cayenne) is used. The ratio of *capsicum* (cayenne) to liquid may be 1:5 if dried herbs are used. If dried *capsicum* (cayenne) is used, preferably it is mixed with a liquid including about 95% alcohol and about 5% water.

In an example, *Hypericum perforatum* (St. John's Wort) may be selected as the herb in the avian tincture. *Hypericum perforatum* (St. John's Wort) may be mixed with a liquid including from about 50% to about 100% alcohol. Preferably, the flowering tops of *Hypericum perforatum* (St. John's Wort) are used. The ratio of *Hypericum perforatum* (St. John's Wort) to liquid may be 1:2 if fresh herbs are used.

In an example, *Monarda fistulosa* (Bee Balm) may be selected as the herb in the avian tincture. *Monarda fistulosa* (Bee Balm) may be mixed with a liquid including from about 50% to about 100% alcohol. Preferably, the leaves and flowers of *Monarda fistulosa* (Bee Balm) are used. The ratio of *Monarda fistulosa* (Bee Balm) to liquid may be 1:2 if fresh herbs are used.

In an example, *Allium sativum* (Garlic) may be selected as the herb in the avian tincture. *Allium sativum* (Garlic) may be mixed with a liquid including from about 50% to about 100% alcohol. Preferably, the bulb of *Allium sativum* (Garlic) is used. The ratio of *Allium sativum* (Garlic) to liquid may be 1:2 if fresh herbs are used.

The herbs may include a combination of Yarrow, St. John's Wort, Yerba Mansa, Yellow Dock and Cayenne. The herbs may include a combination of *Echinacea*, Goldenseal, St. John's Wort and Osha Root. The herbs may include a combination of Yarrow, St. John's Wort and Cayenne. The herbs may include a combination of Osha Root, Bee Balm, Burdock Root and Queen Anne's lace. The herbs include a combination of St. John's Wort, Bee Balm, and Garlic.

The method may further include combining the avian tincture with one or more different avian tinctures into an avian tincture formula. For example, an avian tincture may include a combination of two to six avian tinctures. The ratio of the combination of avian tinctures may be 1:1. The ratio of the combination of avian tinctures may vary. The term avian tincture and avian tincture formula may be used interchangeably in the present teachings.

In an example, the herbs may include a combination of Yarrow, St. John's Wort, Yerba Mansa, Yellow Dock and Cayenne. The avian tincture may include a combination of five different avian tinctures. For example, the formula mix ratio may include 4 parts Yarrow, 4 parts St. John's Wort, 2 parts Yerba Mansa, 1 part Yellow Dock and 1 part Cayenne (e.g. 4:4:2:1:1). The avian tincture may be a bumblefoot remedy. The avian tincture may dissolve abscesses without invasive lancing or cutting open of infected foot pads. The avian tincture may also relieve inflamed and swollen leg joints.

In an example, the herbs include a combination of *Echinacea*, Goldenseal, St. John's Wort and Osha Root. The avian tincture may include a combination of four different avian tinctures. For example, the formula mix ratio may be 1:1:1:1. The avian tincture may be a respiratory issues remedy. The avian tincture may relieve deep respiratory issues in the upper head to lung congestion. The avian tincture may break up congestion and sneezing with mucous discharge. The avian tincture may provide astringent action to dry and soothe inflamed tissue.

In an example, the herbs include a combination of a combination of Yarrow, St. John's Wort and Cayenne. The avian tincture may include a combination of three different avian tinctures. For example, the formula mix ratio may be 1:1:1. The avian tincture may be a wound remedy. The avian tincture may provide a quick-stop bleeding remedy. The avian tincture may also provide bacteriostatic action for wounds, skin abrasions and damaged toenails. The avian tincture may help the wound to quickly form a scab to prevent picking from other birds. The avian tincture may also help internally by bringing help to the wounded site.

In an example, the herbs include a combination of Osha Root, Bee Balm, Burdock Root and Queen Anne's Lace. The avian tincture may include a combination of four avian different tinctures. For example, the formula mix ratio may be 1:1:1:1. The avian tincture may be a sour crop remedy. The avian tincture may provide a remedy for crop infection or sour crop which can occur when the crop does not empty and the food starts to ferment. The avian tincture may provide a remedy for a secondary yeast or bacterial infection resulting from the crop infection or sour crop. The avian tincture may provide a remedy for inflammation causing fluid build-up and crop distention. The avian tincture may provide a remedy to quickly get the crop back to health.

In an example, the herbs include a combination of St. John's Wort, Bee Balm, and Garlic. The avian tincture may include a combination of three avian different tinctures. For example, the formula mix ratio may be 1:1:1. The avian tincture may be an intensive acute care remedy. The avian tincture may be an anti-parasitic. The avian tincture may be an antibacterial. The avian tincture may be an immune builder. The avian tincture may provide antioxidant support for acute disease or parasite overload conditions.

In an example, the herbs include a combination of St. John's Wort and Usnea. The avian tincture may be an antibacterial. The antibacterial avian tincture may include a combination of St. John's Wort and Usnea.

In an example, the herbs include a combination of Garlic, Yerba Mansa and Oregano. The avian tincture may be an anti-inflammatory. The avian tincture may be an antimicrobial. The avian tincture may be both an anti-inflammatory and an antimicrobial. The anti-inflammatory and/or antimicrobial avian tincture may include a combination of Garlic, Yerba Mansa, Oregano and any combination thereof.

In an example, the herbs include a combination of Garlic, Wormwood, and Black Walnut. The avian tincture may be an anthelmintic. Anthelmintic agents are used to eradicate parasitic worms (helminthes) from a host. The anthelmintic avian tincture may include a combination of Garlic, Wormwood, Black Walnut and any combination thereof.

In an example, the herbs include a combination of *Echinacea*, New England Aster, Bayberry and Oregon Grape. The avian tincture may be an expectorant. The avian tincture may be an antimicrobial. The avian tincture may be an astringent. The avian tincture may be an expectorant, antimicrobial, astringent or any combination thereof. The expectorant, antimicrobial, astringent or any combination thereof avian tincture may include *Echinacea*, New England Aster, Bayberry, Oregon Grape and any combination thereof.

In an example, the herbs include a combination of Yellow Dock and Yarrow. The avian tincture may stimulate elimination of waste in the avian digestive system. The waste elimination stimulator avian tincture may include Yellow Dock and Yarrow.

In an example, the herbs include a combination of Cayenne and Ginger. The avian tincture may improve blood circulation. The blood circulation stimulator avian tincture may include Cayenne and Ginger.

In an example, the herbs include a combination of Burdock, *Astragulus*, Stinging Nettle and Tumeric. The avian tincture may be a nutritive. The nutritive avian tincture may include Burdock, *Astragulus*, Stinging Nettle, Tumeric and any combination thereof.

The present teachings also contemplate an avian composition comprising a mixture of least one extracted herb from the group consisting of *Echinacea Purpea/augustifolia* (Purple Coneflower), *Hypericum perforatum* (St. John's Wort), *Ligusticum porter* (Osha Root), *Achillea millifolium* (Yarrow), *Anemopsis californicum* (Yerba Mansa), *Rumex crispus* (Yellow Dock), *Capsicum* (Cayenne), *Monarda fistulosa* (Bee Balm), *Arctium lappa* (Burdock), *Daucus carota* (Queen Anne's Lace), *Allium sativum* (Garlic), Usnea, Oregano, Wormwood, Black Walnut, New England Aster, Bayberry, Oregon Grape, Ginger, *Astragulus*, Stinging Nettle, Tumeric and any combination thereof and about 50% to about 100% alcohol.

The present teachings also contemplate methods for treatment of the avian species with the avian tincture. The method may include administrating an internal dose of a tincture made by the method of the present teachings to a bird. The method may include monitoring health symptoms of the bird. The method may include repeating the internal dose of tincture to the bird over a period of from about 5 to about 10 days. The method for treating the avian species with the avian tincture, may include applying the avian tincture to an external wound or cyst of the bird.

The dose of tincture may be about 1 drop per pound of weight of the bird. The dose of tincture may not exceed about 30 drops of tincture a day. A dose of about 6-10 drops per day may be administered. Preferably, the method includes administering a dose about 6-10 drops per day for birds with a non-acute condition or recovering from an acute illness. A dose of about 6-10 days should be maintained until health is achieved.

The method may include administering a high dose of about 10-15 drops per day. The method may include administering the high dose early in the treatment of the bird. For example, the high dose may be administered on day 1 or day 2 of the treatment. Preferably, the method includes including administering a high dose of about 10-15 drops per day for extremely ill birds. An extremely ill bird may stop eating and drinking. Use of high doses early in treatment may stop the progression of pathogens quickly. The method may include administering the high dose twice a day. Preferably, the high dose is administered until the symptoms recede. A response may be seen and symptoms may lessen within about 1-2 days.

Each drop of the tincture may be diluted with two to three drops of water before administration. Preferably, the dilution is accomplished by mixing the water and alcohol in a small glass and drawing the mixture back up into the dropper. Preferably, the diluted mixture is used immediately.

The tincture is administered to a bird by hooking a fingernail under the top point of the upper beak and pulling back until the mouth is opened. The tincture is administered by squirting the tincture on the bottom of the mouth and tongue. The tincture administration may be followed up by a small dose of water. The tincture may be mixed in a small amount of water and administered in that way.

The present teachings also contemplate a method for treating the avian species with the avian tincture, wherein the method includes applying the avian tincture to an external wound or cyst of the bird. The external method of application may be used in combination with the internal method of application. During external application of the avian tincture, only enough avian tincture to coat the wound or external cyst is used.

In the event, that the bird does not respond to treatment after about 3 days and symptoms of reduced health persist, the formula being used is not the right one for the illness or the illness may have progresses to a fatal point. Other formulas may be tried. The tinctures may not generally be used more than about 5 to about 10 days, as poultry generally recover within that time from most illnesses.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of, or even consist of, the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps. Likewise, any reference to "first" or "second" items is not intended to foreclose additional items (e.g., third, fourth, or more items); such additional items are also contemplated, unless otherwise stated.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints. The specification of ranges herein also contemplates individual amounts falling within the range. Thus, for example, a range of 10 to 15 contemplates individually the amounts of 10, 11, 12, 13, 14, and 15.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

I claim:

1. A method for producing a tincture formula comprising:
   (i) creating a plurality of tinctures, each of the plurality of tinctures produced by:
      a) mixing a ratio of at least one herb with a liquid including 190 proof neutral organic grain alcohol diluted with water into a first container, wherein the herb is a fresh herb or a dried herb;
      b) sealing the first container to provide an air tight environment;
      c) shaking the mixture 2-3 times a day for 2 weeks;
      d) straining the herb material to separate it from the liquid mixture;
      e) pouring the liquid mixture into a second container; and
      f) sealing the second container containing the liquid mixture and storing it; and
   (ii) combining the plurality of tinctures to produce the tincture formula,
      wherein the plurality of tinctures includes: a tincture of *Achillea millifolium* (Yarrow) mixed with a liquid of 50% alcohol and 50% water, a tincture of *Hypericum perforatum* (St. John's Wort) mixed with a liquid of 50% alcohol and 50% water, a tincture of *Anemopsis californicum* (Yerba Mansa) mixed with a liquid including 60% alcohol and 40% water, a tincture of *Rumex crispus* (Yellow Dock) mixed with a liquid of 50% alcohol and 50% water, and a tincture of *capsicum* (Cayenne) mixed with a liquid including 95% alcohol and 5% water;
      wherein the tincture formula composition contains 4 parts Yarrow, 4 parts St. John's Wort, 2 parts Yerba Mansa, 1 part Yellow Dock, and 1 part Cayenne;
      wherein the tincture formula is configured to treat bumblefoot in avian species and dissolves abscesses free of invasive lancing or cutting open of infected areas; and
      wherein the tincture formula further relieves inflamed and swollen leg joints in the avian species.

2. The method of claim 1, wherein the ratio of herbs to liquid is 1:2 for fresh herbs and 1:5 for dried herbs.

3. The method of claim 1, wherein the plurality of tinctures further includes a tincture having the at least one herb, selected from the group consisting of: *Echinacea Purpea/augustifolia* (Purple Coneflower), *Ligusticum porter* (Osha Root), *Monarda fistulosa* (Bee Balm), *Arctium lappa* (Burdock), *Daucus carota* (Queen Anne's Lace), *Allium sativum* (Garlic), and any combination thereof.

4. The method of claim 3, wherein the plurality of tinctures further includes a tincture of *Ligusticum porter* (Osha Root) mixed with a liquid including 70% alcohol and 30% water.

5. The method of claim 3, wherein the plurality of tinctures further includes a tincture of *Monarda fistulosa* (Bee Balm) mixed with a liquid of 50% alcohol and 50% water, and wherein leaves and flowers of the Bee Balm are used to create the tincture.

6. The method of claim 1, wherein the plurality of tinctures further includes a tincture of Oregon Grape mixed with a liquid including 70% alcohol and 30% water.

7. The method of claim 1, wherein the plurality of tinctures further includes a tincture of New England Aster mixed with a liquid including 50% alcohol and 50% water.

8. The method of claim 1, wherein the tincture formula is safe for ingestion by the avian species, and the avian species is intended to be poultry.

9. The method of claim 1, wherein the tincture formula has a shelf life of at least 3 years.

\* \* \* \* \*